(12) United States Patent
Kutyev

(10) Patent No.: US 9,566,379 B2
(45) Date of Patent: Feb. 14, 2017

(54) HANDHELD ORAL IRRIGATOR

(71) Applicants: Anatoly Anatolyevich Kutyev, Moscow (RU); Andrey Vasilyevich Konin, Moscow (RU)

(72) Inventor: Anatoly Anatolyevich Kutyev, Moscow (RU)

(*) Notice: Subject to any disclaimer, the term of this patent is extended or adjusted under 35 U.S.C. 154(b) by 0 days.

(21) Appl. No.: 15/101,547

(22) PCT Filed: Dec. 4, 2014

(86) PCT No.: PCT/RU2014/000905
§ 371 (c)(1),
(2) Date: Jun. 3, 2016

(87) PCT Pub. No.: WO2015/084218
PCT Pub. Date: Jun. 11, 2015

(65) Prior Publication Data
US 2016/0303309 A1    Oct. 20, 2016

(30) Foreign Application Priority Data

Dec. 6, 2013 (RU) ................................ 2013154165

(51) Int. Cl.
| | | |
|---|---|---|
| *A61M 3/02* | (2006.01) | |
| *A61M 11/00* | (2006.01) | |
| *A61M 3/00* | (2006.01) | |
| *A61C 17/02* | (2006.01) | |
| *A61C 17/028* | (2006.01) | |

(52) U.S. Cl.
CPC ........ *A61M 3/0262* (2013.01); *A61C 17/0202* (2013.01); *A61C 17/0205* (2013.01); *A61C 17/028* (2013.01); *A61C 17/0217* (2013.01); *A61M 3/005* (2013.01); *A61M 11/008* (2014.02);
(Continued)

(58) Field of Classification Search
CPC .... A61M 3/02; A61M 3/0262; A61M 1/0058; A61M 1/0072; A61M 2039/0009; A61M 3/005; A61M 1/066; A61M 11/006; A61M 11/008; A61M 2205/075; A61M 2210/0625–2210/0637; A61C 17/02; A61C 17/022; A61C 17/028; A61C 15/00
(Continued)

(56) References Cited

U.S. PATENT DOCUMENTS 2,355,012 A * 8/1944 Reifsnyder ........ A61C 17/0202
433/89
3,199,510 A * 8/1965 Sinai ...................... A61C 17/02
128/200.14
(Continued)

FOREIGN PATENT DOCUMENTS

| EP | 0592082 A1 | 8/1993 |
| RU | 2130325 C1 | 5/1999 |
| WO | 9321856 A1 | 11/1993 |

*Primary Examiner* — Imani Hayman
*Assistant Examiner* — James D Ponton
(74) *Attorney, Agent, or Firm* — Nadya Reingand

(57) ABSTRACT

The invention is directed to providing, at the exit from the nozzle of an irrigator, an intermittent gas-liquid jet for enabling effective cleaning, while being easy to use, A bulb (1) has an aerator introduced therein which is in the form of a tubular element (7) with open tips (71, 72) and a perforation region (73) in the side wall of the element (7), the region having at least one hole. The end of the tubular element (7) on the open-ended side is freely disposed in the cavity of the bulb (1), and the tip (71) is disposed with clearance from the base of the bulb.

3 Claims, 1 Drawing Sheet

(52) U.S. Cl.
CPC  *A61M 2205/075* (2013.01); *A61M 2210/0625* (2013.01); *A61M 2210/0631* (2013.01)

(58) Field of Classification Search
USPC .......................................................... 433/216
See application file for complete search history.

(56)  References Cited

U.S. PATENT DOCUMENTS

| | | | |
|---|---|---|---|
| 2006/0217658 A1* | 9/2006 | Tsutsui .................. | A61M 13/00 604/58 |
| 2011/0087174 A1* | 4/2011 | Carpenter ........... | A61M 3/0262 604/257 |

* cited by examiner

HANDHELD ORAL IRRIGATOR

CROSS REFERENCE TO RELATED APPLICATIONS

The present application is a National stage application from the PCT application PCT/RU2014/000905 filed Dec. 4, 2014, which claims priority to Russian application RU2013154165 filed on Dec. 6, 2013.

FIELD OF THE INVENTION

The invention relates to the medical instruments, namely, to irrigators, and may be employed for hygienic procedures in clinical and domiciliary.

PRIOR ART

The proper hygiene of the oral cavity, teeth and gingivae is known to inhibit development of recalcitrant periodontitis and pertodontosis. Intensive tooth-washing following routine cleaning procedures using a tooth-brush favors removal of food residues, pathogenic germs and other infection-producing components. Known are efficient electronic gadgets for oral cavity irrigator, in particular, that of Waterpik Technologies (USA), employing bubble technology of delivered jet saturation, however, they are featured with a rather complicated design.

A handheld irrigator is known (WO2011105644 (A1), YOO B YUNG EUN, Sep. 1, 2011), comprising a pear-shaped rubber bulb with elastic walls and jet nozzle tip connected to the nozzle through-channel with a tube submerged inside the bulb down to its bottom. However, this irrigator is designed to prevent bulb filling through the nozzle, which is implemented by means of a separate piston pump. Moreover, the irrigator is only intended for caval organ filling with a liquid, without arranging washing thrust. A handheld oral irrigator is described (DE3146729 (A1), AHSBAHS, Jul. 7, 1983), comprising a jet nozzle connected to the tube immersed into a vessel with liquid and a liquid jet interrupter, however, not employing liquid aeration.

An irrigator is known (RU2018323 C1, Mazetov et al., Aug. 30, 1994) comprising a mixer for cleaning liquid and gas generating a gas-liquid medium at the jet nozzle output. The mixer comprises an olive-shaped caval chamber with a central nozzle, a hose, and a gas/air delivery device. The caval chamber in the central nozzle area comprises a tangential nipple for gas delivery device connection, a part of the central nozzle being located within the inner volume of the caval cavity. However, this irrigator is featured with a complicated design and is not intended for using in household and field conditions.

Known from the application (DE19527943 (A1), KERPLAS NEUENBURG GMBH KUNSTST, Feb. 20, 1997) is a device for delivery gas-liquid medium implemented as an elastic bulb rot the liquid with as tube located therein and connected with a jet nozzle installed at the spout. Liquid delivery from the spout is effected at bulb pressing by hand. However, in this device nozzle and tube inner diameter are selected basing on condition of generating of a finely pulverized spray featured by low mechanical impact.

An oral irrigator is known (09321856 (A1), POGLIANI, GRIMOLDI, Nov. 11, 1993), wherein a pulsing liquid jet is generated through using of a jet modulating valve for the liquid outflowing from the bulb pressurized with compressed gas. However, it requires a stock of disposable bulbs, providing no possibility of bulb recharging with the required medium. There are also other oral cavity handheld irrigators described in (U.S. Pat. No. 4,286,735 (A), SNEIDER, Sep. 1, 1981; EP0592082 (B1), NOVADENT LTD, Jan. 13, 1999; BRPI1105928 (A2), DA SILVA HERNANDES, Sep. 10, 2013).

The easiest and the most affordable irrigator for washing of organism canals and cavities is a ball syringe constituting a rubber pear-shaped bulb with elastic walls and soft or rigid tip possessing a through-channel with a jet nozzle suitable for conducting liquid into and out of the bulb (Kabatov, Yu. F., Medical instruments, hardware, and equipment.—Moscow, "Meditsina", 1977, pp. 70 to 73 (in Russian); FIG. 6 thereof is the closest analog). At the same time, the efficiency of the ball syringe irrigator depends strongly on liquid jet pressure head: at high pressure, the jet may injure the gingiva or even cause oral hemorrhage. Besides, the ball syringe having been filled once is featured by a continuous outflowing liquid jet on applying one-time compression force to its ball and does not generate a gas-liquid jet, which is preferable as described above.

DISCLOSURE OF THE INVENTION

The present invention is aimed at perfection of an oral handheld irrigator.

The irrigator is embodied as a pear-shaped bulb for liquid with elastic walls and comprises, on its tapered end, a tip connected to a jet nozzle by a through-channel.

An aerator is comprised, in the bulb constituting a tubular element with open butts and side surface with a perforated area. One end of the tubular element is fixed in the through-channel from the nozzle side with its butt open inside the jet nozzle. The other end is located loosely in the bulb cavity with its butt having a gap with respect to the bulb bottom, the perforated area in the side wall of the tubular element being located inside the bulb cavity adjacent to the tip tapered end. The irrigator may be characterized in that the tubular element is embodied as a component integral with the rigid tip, and that the size of the perforated area constitutes 0.05 . . . 0.6 of the flow cross-section of the tubular element. The irrigator may be also characterized in that the length of the tubular element constitutes 0.75 . . . 0.98 of the distance between the bottom and the jet nozzle along the irrigator symmetry axis. The irrigator may be also characterized in that it additionally comprises as back-flow valve installed in the bulb wall and embodied in the manner providing filling the bulb cavity with air and/or liquid when recovering its shape on bulb release.

The technical result of the invention consists in providing on the handheld irrigator jet nozzle exit of an intermittent gas-liquid jet promotion efficient cleaning, maintaining at the same time simplicity in design and operation.

THE PREFERRED EMBODIMENT OF THE INVENTION

Figure 1:
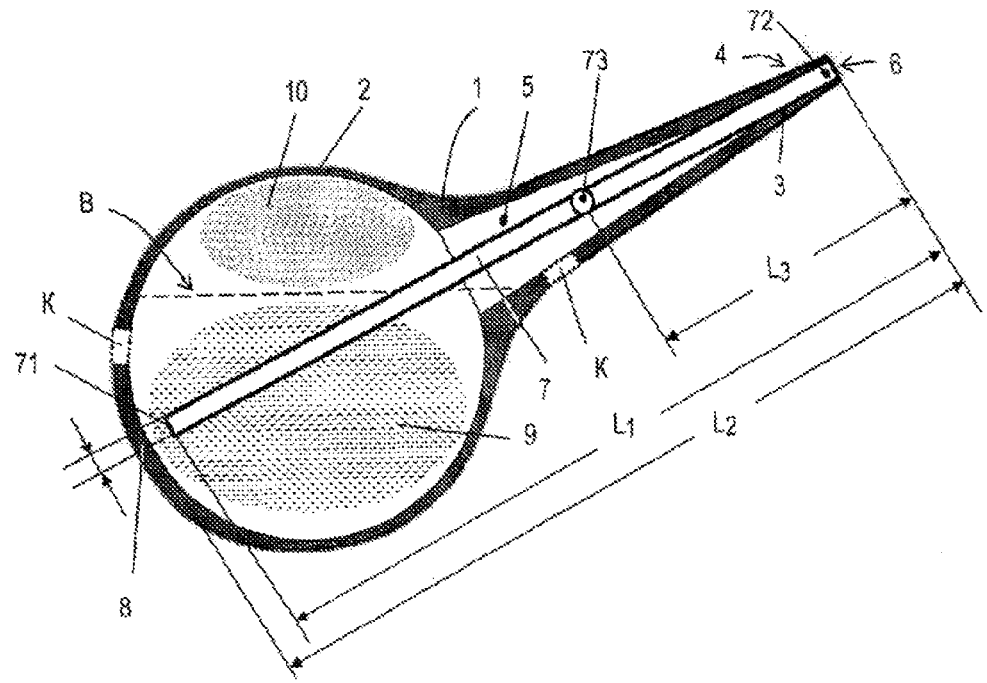
FIG. 1 shows the design of the claimed device.

The irrigator is embodied as a pear-shaped bulb 1 with elastic walls 2 and comprises, on its tapered end 3, a soft or rigid tip 4 connected by a through-channel 5 to a jet nozzle 6.

An aerator is comprised in the bulb 1 constituting a tubular element 7 with open butts 71, 72 and a perforated area 73 in the side surface of the element 7 formed by at least one orifice.

The open end of the tubular element 7 from the nozzle side is installed loosely in the cavity of the bulb 1, its butt 71 having a gap with respect to the bulb bottom. Length $L_1$ of the tubular element is smaller than the distance $L_2$ between the bottom and the jet nozzle along the irrigator symmetry axis and constitutes $L_1=(0.75 \ldots 0.98)*L_2$, that is, the open butt 71 is installed with a gap with respect to the bulb 1 bottom 8.

The end of the tubular element from the side of the open butt 72 is leak-proof fixed in the through-channel 5 of the tip tapered end 3 in the manner that its butt is open towards inside of the jet nozzle 6. This means that the butt 72 is installed flush or with depression with respect to the nozzle 6 and never protrudes beyond its limits. This prevents an immediate contact of the butt 72 with the oral cavity being irrigated when using a soft-tip bulb.

The perforated area 73 in the side wall of the tubular element 7 is located inside the bulb 1 cavity adjacent to the tip tapered end at the distance $L_3$ from the butt 72, this distance being chosen experimentally for each bulb dimension-type. The size of the perforated area 73 constitutes 0.05 . . . 0.6 of the flow cross-section (diameter) of the tubular element 7.

If the bulb 1 comprises a rigid tip 4, then the tubular element may be embodied integrated with the tip in a single mold. In this case, the tubular element may protrude beyond the nozzle 6, and the tip 4 itself must be chamfered as it is usually done in commercial ball syringes.

The irrigator may comprise a back-flow valve K installed in the bulb 1 wall and embodied in the manner providing filling the bulb cavity with air and/or liquid when recovering its shape on bulb release due to the elasticity. Dotted lines in the figures show schematically installation points for the back-flow valve K, the precise locations of valve installation being not critical.

When the irrigator operated in the suction mode and tip 4 is immersed in a vessel with liquid, valve K opens, and the inflow may occur through both tip 4 and valve K, so air or liquid enter inside. When the bulb 1 is compressed, valve K closes, and the gas-liquid mixture is ejected only through the tip 4 with the nozzle 6.

Figure 2:
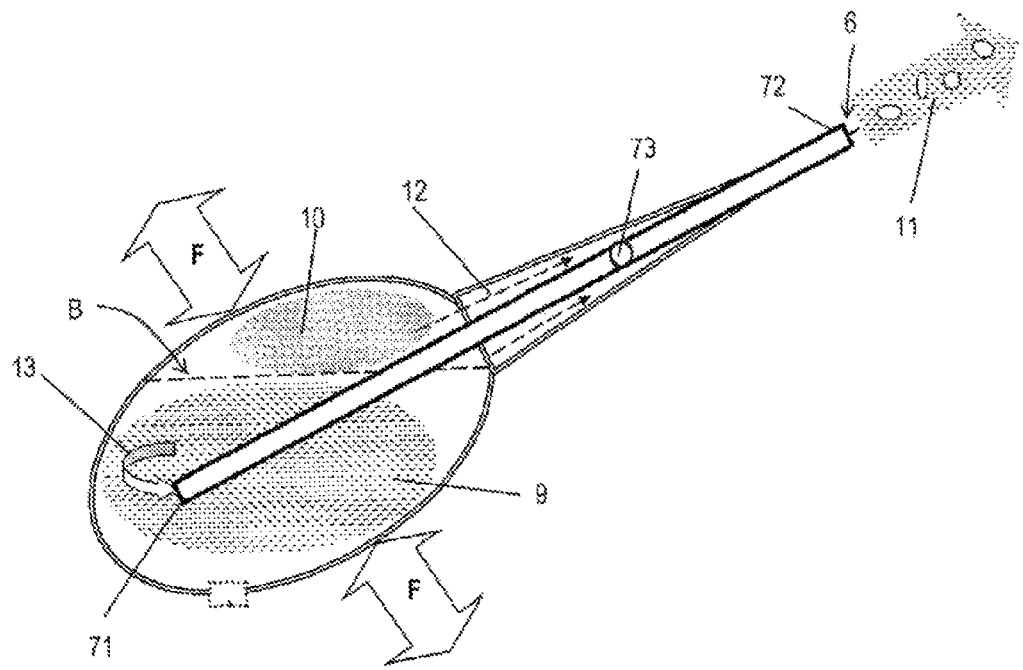
FIG. 2 illustrates the operational principle of the claimed device.

The claimed device is used as follows (see also FIG. 2):

The irrigator is filled with a cleaning liquid 9 in a conventional manner, for example, the tip of the compressed bulb is immersed in the vessel with the solution, after which the bulb is released. This process is always accompanied by intake of a certain amount of the air 10, always existing above the liquid (their interface 'B' is shown in the dotted line).

After this, the tip with the nozzle 6 is brought to the cavity being cleaned, for example, to an interdentium or a gingival crevice, and the bulb 1 walls are pronouncedly and repeatedly compressed (illustrated by arrows 'F'). The ergonomic position of the irrigator is with tip 4 oriented horizontally or slightly raised. Air 10 in the irrigator cavity accumulated in its tapered end 3 (air flow is schematically shown with the dotted arrow 12) is admixed through the perforated area 73, for example, the orifice, to the pressurized liquid 9 (arrow 13) delivered through the orifice in the butt 71 of the tubular element 7. This results in generating on the exit of the nozzle 7 of an intermittent gas-liquid jet 11. The obtained gas-liquid jet possesses improved cleaning capabilities. In the case of the irrigator tip 4 with the nozzle 6 is brought immediately adjacent to the interdentium, then the irrigator would operate not only as an efficient source of the gas-liquid medium, but also as a pump the food residues would be flushed and sucked by the same nozzle 6, which, however, would require additional cleaning of the device.

INDUSTRIAL APPLICABILITY

The irrigator is embodied out of materials commonly employed in medical industry. The tests demonstrated that, provided retaining simple design and convenience of usage, the irrigator generates at the exit of its nozzle an intermittent gas-liquid jet contributing to the efficient cleaning of the interdentium.

What is claimed is:

1. A handheld irrigator, consisting of:
    an enema-shaped body consisting of a pear-shaped bulb with elastic walls with a tapered tip attached to the bulb; the pear-shaped bulb being configured to be partially filled with a liquid;
    a tubular element placed inside the body;
    the tubular element having a first end being sealingly fixed to an internal surface of the tip at a narrowest part of the tip;
    a second end of the tubular element being installed with a gap between the second end and a bulb bottom,
    the tubular element having an orifice in a portion of the tubular element located in the tapered tip;
    a cross-sectional area of the orifice being 0.05 to 0.6 times a cross-sectional area of a lumen of the tubular element;
    the irrigator producing a gas-liquid flow while squeezing the bulb with a hand; the gas-liquid flow being a jet with a force sufficient to remove unwanted objects between teeth;
    the jet force being determined by a ratio between the cross-sectional area of the orifice and the cross-sectional area of the lumen of the tubular element.

2. The irrigator of claim 1, wherein the tip and the tubular element are molded together as a single mold.

3. The irrigator of claim 1, wherein a length of the tubular element is 0.75 to 0.98 times a distance between the bulb bottom and a jet nozzle.

* * * * *